(12) United States Patent
Yasuzawa et al.

(10) Patent No.: US 9,645,161 B2
(45) Date of Patent: May 9, 2017

(54) SAMPLE INSPECTION AUTOMATION SYSTEM

(75) Inventors: Kenichi Yasuzawa, Tokyo (JP); Koji Kamoshida, Tokyo (JP); Masashi Akutsu, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 437 days.

(21) Appl. No.: 14/238,615

(22) PCT Filed: Sep. 6, 2012

(86) PCT No.: PCT/JP2012/072791
§ 371 (c)(1),
(2), (4) Date: Feb. 26, 2014

(87) PCT Pub. No.: WO2013/042549
PCT Pub. Date: Mar. 28, 2013

(65) Prior Publication Data
US 2014/0208872 A1 Jul. 31, 2014

(30) Foreign Application Priority Data

Sep. 20, 2011 (JP) .................. 2011-204047

(51) Int. Cl.
*G01N 35/04* (2006.01)
*G01N 35/00* (2006.01)

(52) U.S. Cl.
CPC ......... *G01N 35/04* (2013.01); *G01N 35/0092* (2013.01); *G01N 35/00732* (2013.01);
(Continued)

(58) Field of Classification Search
None
See application file for complete search history.

(56) References Cited

U.S. PATENT DOCUMENTS

| 5,623,415 A | 4/1997 | O'Bryan et al. |
| 6,319,718 B1 | 11/2001 | Matsubara et al. |

(Continued)

FOREIGN PATENT DOCUMENTS

| JP | 07-234228 A | 9/1995 |
| JP | 08-122337 A | 5/1996 |

(Continued)

OTHER PUBLICATIONS

International Preliminary Report on Patentability received in International Application No. PCT/JP2012/072791 dated Apr. 3, 2014.
(Continued)

*Primary Examiner* — Robert R Raevis
(74) *Attorney, Agent, or Firm* — Mattingly & Malur, PC

(57) ABSTRACT

There is provided a sample inspection automation system which uses a single holder as its carrier, which can supply empty holders to a distant processing unit on an extended circling path without delay, and which permits continuous operation in case of a failure through detachment of a failed part for example. The system combining a plurality of processing units has an empty holder circling path with a mechanism to circle empty holders across all processing units within the system in unicursal fashion; stoppers for retaining empty holders on the circling path; and a mechanism for controlling the stoppers on the circling path given an empty holder request from a processing unit. The empty holder circling path is made of a plurality of loops each equipped with the stopper. The sample inspection automation system thus configured supplies empty holders efficiently and simplifies system operation through fallback operation.

10 Claims, 3 Drawing Sheets

(52) U.S. Cl.
CPC ........... *G01N 2035/0094* (2013.01); *G01N 2035/0462* (2013.01); *G01N 2035/0465* (2013.01); *G01N 2035/0467* (2013.01); *G01N 2035/0491* (2013.01)

(56) References Cited

U.S. PATENT DOCUMENTS

| | | |
|---|---|---|
| 7,842,237 B1 | 11/2010 | Shibuya et al. |
| 2012/0177547 A1 | 7/2012 | Fukugaki et al. |
| 2013/0125675 A1* | 5/2013 | Muller et al. ............. 73/864.23 |

FOREIGN PATENT DOCUMENTS

| | | |
|---|---|---|
| JP | 09-236608 A | 9/1997 |
| JP | 11-500224 A | 1/1999 |
| JP | 3059194 U | 3/1999 |
| JP | 2000-74925 A | 3/2000 |
| JP | 2001-141732 A | 5/2001 |
| JP | 2002-357612 A | 12/2002 |
| JP | 3618067 B2 | 11/2004 |
| JP | 2005-156196 A | 6/2005 |
| JP | 2007-309675 A | 11/2007 |
| JP | 2010-175513 A | 8/2010 |
| NL | 1015304 C2 | 11/2001 |
| WO | 96/25712 A1 | 8/1996 |
| WO | 2011/040197 A1 | 4/2011 |
| WO | 2011/142182 A1 | 11/2011 |
| WO | 2012/043261 A1 | 4/2012 |

OTHER PUBLICATIONS

Extended European Search Report received in corresponding European Application No. 12833779.7 dated Mar. 27, 2015.

* cited by examiner

FIG. 1
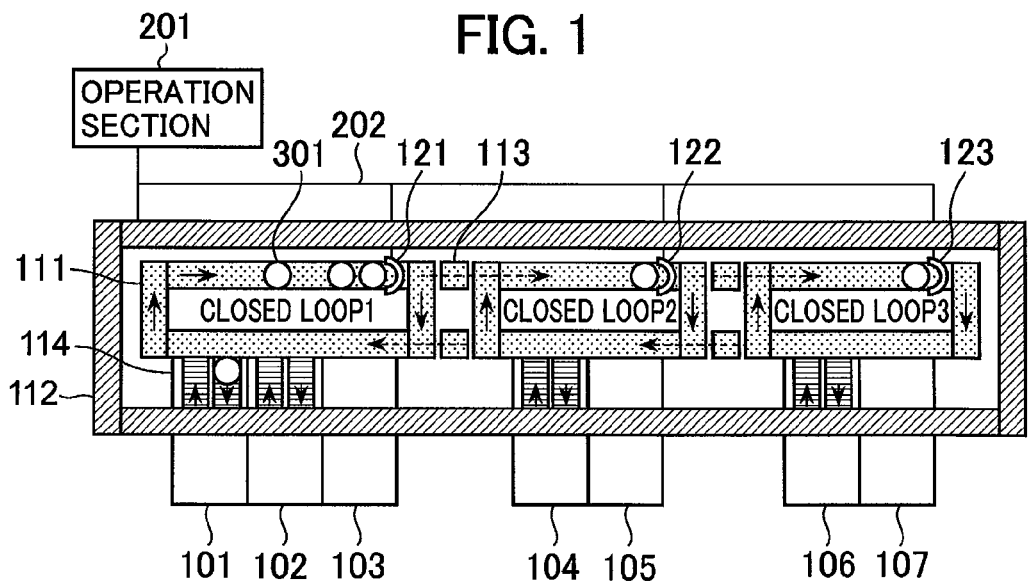
FIG. 2
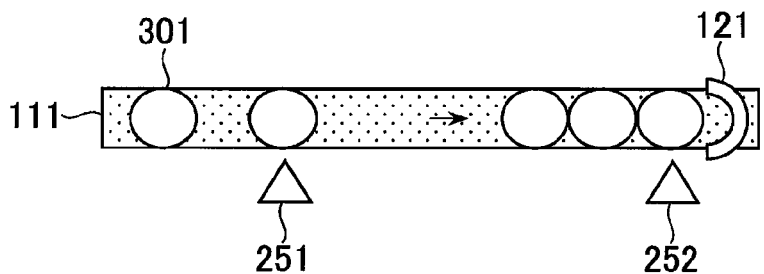
FIG. 3
| STOPPER SETTING PARAMETERS | | |
|---|---|---|
| STOPPER INFORMATION | | |
| STOPPER ID | SENSOR POSITION | MAXIMUM NO. OF RETAINED HOLDERS |
| STOPPER121 | 51 | 30 |
| STOPPER122 | 52 | 10 |
| STOPPER123 | 53 | 15 |

FIG. 6

| CLOSED LOOP OFFLINE SETTING PARAMETERS | |
|---|---|
| CLOSED LOOP OFFLINE INFORMATION | |
| CLOSED LOOP NO. | OFFLINE |
| 21 | ☐ |
| 22 | ☑ |
| 23 | ☐ |

SAMPLE INSPECTION AUTOMATION SYSTEM

TECHNICAL FIELD

The present invention relates to a sample inspection automation system that processes samples such as blood and urine in clinical inspection.

BACKGROUND ART

When a sample such as blood or urine is to be analyzed by automatic analyzers in clinical inspection, there can be diverse kinds of preprocessing to be performed depending on the details of the request for the inspection, such as centrifugation of the sample, dispensing of the sample into dedicated containers for each automatic analyzer, and pasting of barcode labels or the like onto the sample containers. Many hospitals, inspection centers and like institutions have introduced sample inspection automation systems that perform these kinds of preprocessing automatically for economizing on manpower and improving efficiency.

The containers containing samples such as blood or urine are mounted on a carrier called a rack or a sample container holder that transports one or a plurality of sample containers to the sample inspection automation system. Depending on the inspection items to be measured and the details of the preprocessing, the samples are each subjected to diverse processes: centrifugation of the sample; an uncapping process for opening the cap of each container; a dispensing process that involves dispensing the sample into at least one other container (i.e., dispensing from a parent sample container into child sample containers); a labeling process for pasting barcode labels onto the child sample containers; a capping process for closing the cap on each child sample container; a classification and storage process for classifying the parent and child samples preparatory to subsequent processes, and an analysis and measurement process for transporting a child sample rack to an automatic analyzer for analysis and measurement of child samples, among others. Apparatuses equipped with the functions for carrying out these processes are connected by a plurality of transport lines in a manner constituting a sample inspection automation system.

A sample inspection automation system that uses a single holder as its carrier performs the process of switching actual samples with empty holders on a plurality of processing units. For example, when samples introduced on a batch basis are to be mounted onto a holder, when centrifuged samples are to be moved from a centrifugation bucket to a holder, or when child samples prepared by a child sample dispensing process are to be mounted onto a holder, it is necessary to supply each processing unit with an empty holder for holding the sample containers involved. If the process of supplying holders is not carried out quickly, the processing speed of the sample inspection automation system as a whole tends to be lowered.

As one way of supplying racks or holders to the sample inspection automation system, there exists a known method involving setting a large quantity of sample racks beforehand on the apparatuses in order to deal with sample-specific processes, as described in Patent Document 1, for example.

According to Patent Document 2, the installation area for a large quantity of sample racks is reduced by mounting a predetermined number of sample racks on trays that are disposed in multi-layered fashion in a sample rack supply section and a sample rack recovery section, the sample racks being supplied and recovered by means of vertically driven elevator mechanisms.

Patent Document 3 describes a method whereby apparatuses are connected to an endless-type transport line that allows sample racks to be used repeatedly by the apparatuses.

Patent Document 4 discloses a sample inspection automation system in which a dedicated empty holder transport line is set up apart from a sample transport line so that empty holders can be supplied to each processing unit as needed.

PRIOR ART DOCUMENTS

Patent Document

Patent Document 1: JP-3618067-B
Patent Document 2: JP-2007-309675-A
Patent Document 3: JP-H08-122337-A
Patent Document 4: WO2011/040197

SUMMARY OF THE INVENTION

Problem to be Solved by the Invention

The methods described in the above-cited Patent Documents 1 and 2 require preparing as many sample racks as a large number of samples to be processed, which inevitably entails causing the system to become larger in size and more complex. Also, before using the system, the operator has to deal with the chore of replenishing a large quantity of sample racks.

The method of Patent Document 3 involves reusing the sample racks while getting the sample rack transport line looped within the system, so that there is no need for a large number of sample racks. However, because empty racks and sample-loaded racks transit on the same transport line, congestion can occur on the transport line. This makes it difficult to build a system operating at high processing speeds. Also required inevitably are complex transport controls, such as having to distinguish between empty racks and sample-loaded racks.

The method described in Patent Document 4 can avert the problems disclosed in the above-cited Patent Documents 1 through 3. However, the empty holder circling path is structured singly to transit all processing units. This means that depending on where the processing unit of interest is located, it may have to wait for empty holders to arrive after transit through almost the entire circumference of the circling path. It follows that it takes long for empty holders to be supplied to the desired processing unit that may remain depleted having to wait for the holders to arrive. Furthermore, if part of the sample inspection automation system fails, or if the entire system has become incapable of operating continuously, the empty holder supply method disclosed in Patent Document 4 has difficulty taking countermeasures such as detachment of an affected unit from the system.

In order to solve these problems of the past, one object of the present invention is to provide a sample inspection automation system having an empty holder circling path configured with a plurality of loop transport paths each equipped with an empty holder stopper in such a manner that the physical distance between each stopper and each processing unit configured is limited to shorten the time required to supply empty holders.

Another object of the present invention is to provide a sample inspection automation system that supplies empty holders quickly to a plurality of processing units in need thereof so that each processing unit will not be depleted of holders.

A further object of the present invention is to provide a sample inspection automation system that can continue operating in case of a failure through detachment of the affected part, for example.

Means for Solving the Problem

In order to attain the above objects, the present invention is constituted as follows:

There is provided a sample inspection automation system including: a plurality of processing units; a main transport path which transports holders loaded with samples to be processed in the plurality of processing units; an empty holder transport path which transports sample-free empty holders; and a supply means which supplies the holders on the empty holder transport path to the processing units or to the main transport path. The empty holder transport path is formed with a plurality of loop transport paths disposed in a looped manner.

In accordance with the practical configuration of a laboratory that utilizes this system, the processing units may be equipped with a group of necessary devices to form a sample inspection automation system capable of dealing with diverse processes. Whereas this description has no reference to details of the above-mentioned processing units, the scope of implementation of the present invention are not relevant to all processing units.

Effects of the Invention

The sample inspection automation system adopting the present invention supplies empty holder without delay to each of the processing units even along an extended circling path. The system further permits continuous operation in case of a failure through detachment of the affected part, for example.

BRIEF DESCRIPTION OF THE DRAWINGS

FIG. 1 is a block diagram showing a typical configuration of a sample inspection automation system.

FIG. 2 is a block diagram showing a typical structure of a sensor that detects the holders retained by a stopper.

FIG. 3 shows a typical screen of an operation section for setting the number of empty holders to be retained by each stopper.

FIG. 6 shows a typical screen of the operation section for setting an offline loop.

MODES FOR CARRYING OUT THE INVENTION

Figure 4:
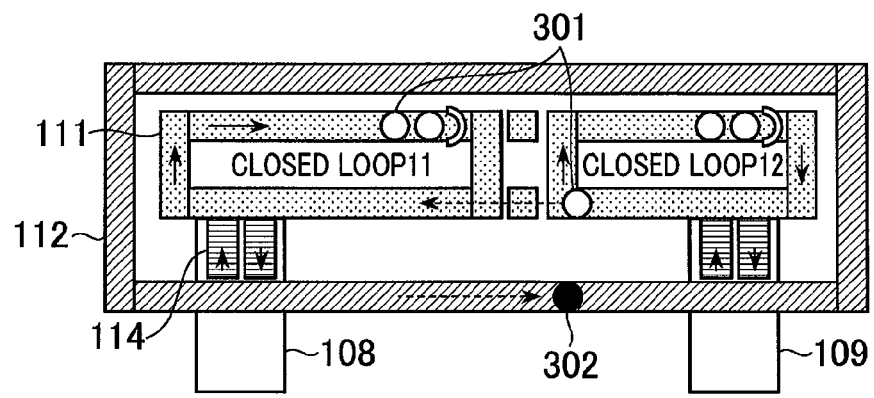
FIG. 4 is a block diagram showing a typical system configuration in which a holder loaded with an actual sample is switched with an empty holder between the control territories of loops.

Some embodiments of the present invention are explained below using the accompanying drawings.

FIG. 1 is a block diagram showing a typical configuration of a sample inspection automation system as one embodiment of the present invention.

The sample inspection automation system shown in FIG. 1 is configured with processing units 101 through 107. An empty holder line 111 is provided to circle empty holders in a manner connecting these processing units 101 through 107. Outside the empty holder line 111 is a sample transport line 112 that holds and transports actual samples. Supply lines 114 that supply empty holders to a processing unit in need thereof connect the empty holder line 111 with the sample transport line 112.

In the example of FIG. 1, loops 1 through 3 are provided. Mini lines 113 connect the loop 1 with the loop 2, and the loop 2 with the loop 3. The loops 1 through 3 are equipped with empty holder stoppers 121 through 123 respectively to stop and retain empty holders 301 on the empty holder line 111.

Also provided is an operation section 201 that controls the empty holder line 111, sample transport line 112, mini lines 113, supply lines 114, and empty holder stoppers 121 through 123. A communication means 202 is provided to ensure communication between the lines and the stoppers.

The empty holders 301 are retained on the empty holder line 111 making up one of the loops by the empty holder stoppers 121 through 123 provided on the line 111.

Although details are not shown in FIG. 1, the processing units 101 through 107 and more processing units may be composed of diverse processing devices in accordance with the operation needs of the laboratory.

FIG. 2 is a partially enlarged example view of the empty holder line of the loop 1 shown in FIG. 1. As with the case in FIG. 1, empty holders 301 moving along the empty holder line 111 are stopped and retained by the empty holder stopper 121. A full state sensor 251 is provided to detect whether a sufficient quantity of empty holders are retained by the empty holder stopper 121, and a depleted state sensor 252 is provided to detect whether the empty holders 301 are depleted. The other loops, not shown, are likewise configured with their stoppers.

The operation section collects these items of detected information from the stoppers of the loops via the communication means 202, and instructs the empty holder line to transfer empty holders between the loops as needed. Specifically, the stopper detected by the full state sensor 251 is instructed to open itself to let empty holders be brought out. This prevents empty holders from getting piled up lopsidedly in a certain loop and avoids getting some loops filled with empty holders and delaying their movements.

Also, holders are expected to be depleted from the loop in which is positioned the stopper detected by the depleted state sensor 252. Thus the stoppers other than the detected stopper are instructed to open. This allows the depleted loop to be supplied with empty holders from the other loops.

The setting of whether or not the number of empty holders retained in each loop is sufficient may be changed depending on the type of the processing unit connected to each loop via the supply line. For example, whereas the quantity of holders needed by a dispensing unit or the like remains constant, an input unit or the like needs a large quantity of holders at the time samples are input but requires few holders to be supplied thereafter. A control section may store information about the necessary holder quantities for these processing units based on their characteristics and adjust the quantity of holders retained between the loops on the basis of the stored necessary holder quantity information and the output from the sensors. There may be provided a screen display allowing the operator to set such necessary holder quantity information.

FIG. 3 shows an example in which the number of empty holders to be retained by each stopper can be set on a screen of the operation section.

A parameter setting screen 801 enables the maximum number of empty holders 802 to be set per stopper. Based on the settings, the operation section monitors and controls the stoppers in operation. For example, the empty holder stopper 122 may be set to retain a maximum of 10 empty holders. Given that setting, if there exist 20 empty holders in the loop furnished with the empty holder stopper 122, the empty holder stopper 122 may be opened to transfer empty holders to other stoppers or to supply empty holders preferentially to each processing unit. On the other hand, if there exist only two empty holders in the loop equipped with the empty holder stopper 122, the empty holder stopper 121 or 123 may be controlled to be opened to supply holders to the loop furnished with the stopper 122.

The number of holders that can be retained by each stopper may be controlled to be changed using a specific logic. For example, if the operator inputs a large quantity of samples to the input unit, the unit needs a large number of empty holders to be loaded with the samples. In that case, adjustments may be made to increase the number of holders to be retained in the loop that supplies holders to the input unit. Similarly, a centrifugal unit requires a relatively large quantity of holders at intervals of a predetermined time period (about 20 minutes) per centrifugation process. In this case, adjustments may be made to raise the number of holders to be retained in the loop that supplies holders to the centrifugal unit.

As described above, where the number of necessary holders varies with the timing, there may be provided a screen that allows the operator to set beforehand the timings and time intervals at which holders are needed by specific processing units. The number of holders to be retained in the loops may also be controlled based on signals received from the configured processing units. For example, there may be conceived a case where a centrifugation process termination time is received from the centrifugal unit together with the number of samples brought out of that unit, the received information being used as the basis for controlling in real time the number of holders to be retained in the loops.

While the sample inspection automation system is in operation, empty holders are continuously brought into and out of the loops so that the number of holders managed per loop is kept varied. Still, the operation section may control empty holders in such a manner that once an ideal number of holders to be stored by each stopper is set beforehand, the ideal holder count may be approximated as closely as possible before system operation is started or when the number of samples to be processed starts to drop so that a stable state is getting reached during system operation.

Otherwise, the sample inspection automation system often has a sample-loaded holder 302 transported along the sample transport line 112 out of the control territory of a loop 11 into that of a loop 12 (see FIG. 4). This state signifies that one holder has been removed from the loop 11. Thus the control section may control the empty holder transport line in such a manner that with one sample-loaded holder transported, an empty holder 301 is brought from the loop 12 into the loop 11.

Once their samples have been processed, the sample-loaded holders 302 are recovered as empty holders into the loops. This arrangement makes it possible to maintain an averaged quantity of empty holders 301 in each loop approximately at all times.

Figure 5:
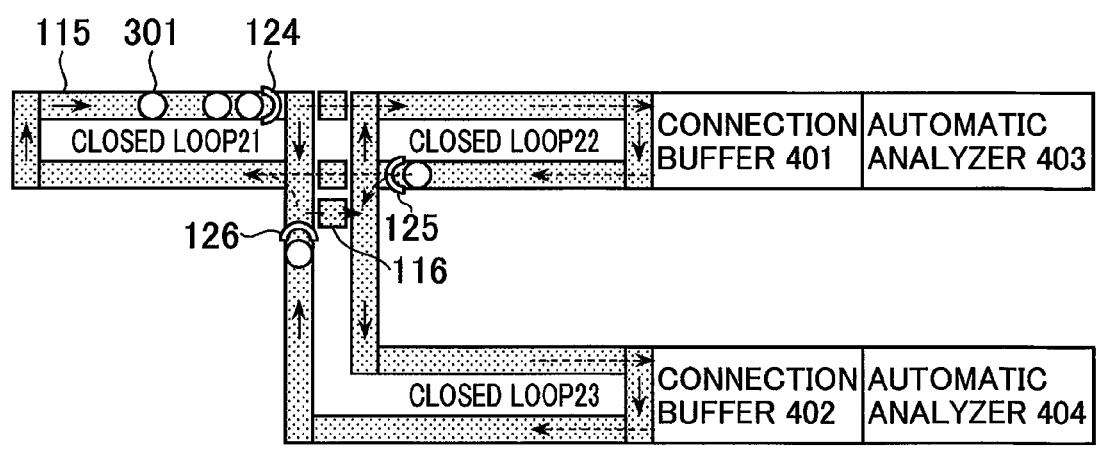
FIG. 5 is a block diagram showing a typical loop configuration of a sample inspection automation system connecting a plurality of automatic analyzers.

FIG. 5 shows another embodiment of the present invention.

In this embodiment, a plurality of automatic analyzers 403 and 404 are connected in parallel with the sample inspection automation system. The empty holder transport line supplying empty holders to the sample inspection automation system is configured with loops 21, 22 and 23. Although three loops make up the empty holder transport line of this embodiment, more loops may be included to constitute the transport line.

The three loops 21 through 23 are furnished with empty holder stoppers 124, 125 and 126, respectively, each positioned immediately upstream of a junction section. Between the loop 23 and the junction section, mini lines 116 are provided to form the loops.

The automatic analyzer 403 is connected to the sample inspection automation system via a connection buffer 401 installed at the end of the loop 22. The connection buffer 401 is intended to permit the process of loading the sample from a single holder (used as a carrier by the sample inspection automation system) onto a rack as a carrier (not shown, used by the automatic analyzer 403), and the process of reloading the sample from the rack (not shown) onto the single holder. It follows that if the single holder for use by the sample inspection automation system can also be used as the carrier by the automatic analyzer 403, then the connection buffer 401 may be considered unnecessary.

A connection buffer 402 and an automatic analyzer 404 are installed at the end of the loop 23 in the same manner as the connection buffer 401 and automatic analyzer 403.

In this respect, there may be conceived a sample inspection automation system in which some inspection items of the automatic analyzers 403 and 404 overlap therebetween. However, such a system is not directly relevant to the present invention and thus will not be discussed further.

Although FIG. 5 does not indicate the main transport line that holds and transports actual samples, the system in practice is obviously equipped with that line.

Whereas the loops 21 through 23 in FIG. 5 are furnished with supply lines that supply empty holders to a plurality of processing units, not shown, these processing units with regard to the loops will not be discussed further because the relations therebetween are substantially the same as those between the processing units 101 through 107 and the loops as described in the foregoing paragraphs.

The system in FIG. 5 is configured with the junction section installed on the empty holder transport line in such a manner that the loops 22 and 23 correspond to the automatic analyzers 403 and 404, respectively. If it is desired for the entire system to keep operating while bringing a certain automatic analyzer offline, the automatic analyzer to be stopped and the loop connected thereto may be handled as one group to be set temporarily offline. This arrangement permits a partial halt of system operation.

An example is explained below in which the measurement of the automatic analyzer 403 and the operation of the processing unit connected to the loop 22 are to be stopped while the analysis of the automatic analyzer 404 is allowed to continue. In this case, the connection buffer 401 connected to the automatic analyzer 403 is stopped, and the loop 22 is detached from the loops 21 and 23. This makes it possible selectively to stop only the automatic analyzer 403 and the processing unit of the loop 22 while the processing units connected to the loops 21 and 23 as well as the automatic analyzer 404 are allowed to keep operating.

If one of the automatic analyzers fails for some reason, detaching it from the system in the form of a unit group constituting a loop allows the normal units to continue operating on a partial basis. Such partial operation may be called fallback operation. As with the above-described offline setting, the system may be partially operated intentionally in "fallback operation" in accordance with the operation needs of the laboratory and irrespective of system trouble. For example, in a laboratory operating 24 hours per day, only some units and some loops may be operated in this manner in nighttime or holiday mode.

What follows is an explanation of the loop configuration. In its minimum setup, each loop may be configured with one stand-alone processing unit. In this case, one loop is considered equal to one processing unit, which makes it possible to detach each of the configured processing units. However, if the loops were configured in such a minutely segmented manner, they would be individually isolated from one another. In practice, it is preferred that each loop be configured with a minimum group of processing units that will permit system operation. For example, if the sample inspection automation system is made up of an input unit, a cap opening unit, a centrifugal unit, a child sample dispensing unit, a cap closing unit, a classification unit, a storage unit, an analysis unit, and a buffer, then the first loop (loop 21 in FIG. 5) may preferably be composed of processing units dealing with "preprocessing," with the second loop, third loop, etc., (loops 22 and 23 in FIG. 5) formed per connection buffer of the analysis unit.

An empty holder released by the empty holder stopper 124 of the loop 21 being opened is supplied either to the processing unit connected to the loop 21 via the supply line or to the loop 22. Which of the destinations the empty holder is supplied to is determined by a junction unit attached to the junction section. Likewise, an empty holder released by the empty holder stopper 125 of the loop 22 being opened is supplied either to the processing unit connected to the loop 22 via the supply line or to the loop 23. Also, an empty holder released by the empty holder stopper 126 of the loop 23 being opened is supplied either to the processing unit connected to the loop 23 via the supply line or to the loop 21. The ON/OFF operations of these stoppers are performed in coordination with one another under the instructions from the operation section.

FIG. 6 shows an example in which a screen of the operation section enables the above-described offline setting to be carried out.

An offline setting screen 803 permits each of the loops to be set offline. Based on these settings, the operation section issues online/offline switching instructions to each of the loops. In this screen example, the loop 22 with its check box checked is shown to be set offline.

Whereas the screen example above was shown as a relatively simple screen layout in which each loop is given a setting field of a single row, there may also be provided an example in which a reduced view of the system configuration diagram such as one shown in FIG. 5 is presented on the screen so that the loop to be set offline may be directly selected from the screen.

Whereas each loop was shown to be set in the screen example above, each processing unit may be set instead. In this case, the loop including the processing unit thus set may conceivably be provided as a target for getting set offline.

The above-described embodiments of the sample inspection automation system offer the following benefits:

In the sample inspection automation system, it is possible to supply empty holders to each processing unit even along an extended circling path. In case of a failure, the operation of the system can be continued by detaching the affected part for example.

DESCRIPTION OF REFERENCE CHARACTERS 1-3, 11, 12, 21-23: Loop
101-109: Processing unit
111, 115: Empty holder line
112: Sample transport line
113,. 116: Mini line
114: Supply line
121-126: Empty holder stopper
201: Operation section
202: Communication means
251: Full state sensor
252: Depleted state sensor
301: Empty holder
302: Sample-loaded holder
401, 402: Connection buffer
403, 404: Automatic analyzer
801, 802: Parameter setting screen
803, 804: Offline setting screen

The invention claimed is:

1. A sample inspection automation system comprising:
a plurality of processing units;
a main transport path which transports holders loaded with samples to be processed in said plurality of processing units;
an empty holder transport path which transports sample-free empty holders, said empty holder transport path being formed with a plurality of loop transport paths;
a supply means which supplies the holders on said empty holder transport path to said processing units or to said main transport path; and
a stopper which stops a plurality of holders collectively on a part of said loop transport paths,
wherein said loop transport paths forming said empty holder transport path are each equipped with at least one of said supply means.

2. A sample inspection automation system according to claim 1, further comprising:
said plurality of loop transport paths including a first loop transport path and a second loop transport path disposed adjacent to said first loop transport path, and
a controller configured to control transport of the holders on said first loop transport path either to a supply means attached to said first loop transport path or to said second loop transport path.

3. A sample inspection automation system according to claim 2, further comprising a plurality of unit groups including:
a first unit group supplied with holders from said first loop transport path, and
a second unit group which has functionality different from that of said first unit group and which is supplied with holders from said second loop path.

4. A sample inspection automation system according to claim 1, further comprising a sensor which detects the number of holders being stopped by said stopper.

5. A sample inspection automation system according to claim 4, wherein said sensor detects whether the number of holders being stopped by said stopper falls within a predetermined holder count range.

6. A sample inspection automation system according to claim 5, further comprising a control section which, if the number of holders being stopped by said stopper does not fall within the predetermined range, then transports holders from an adjacent loop transport path to the loop transport path furnished with the stopper in question.

7. A sample inspection automation system according to claim 6, wherein
said plurality of processing units are made up of a plurality of processing unit groups including a first processing unit group supplied with holders from said first loop transport path and a second processing unit group supplied with holders from said second loop transport path, and
said main transport path transports sample-loaded holders between said plurality of processing unit groups, said control section performing control in such a manner that if as many as n holders are transported from said first processing unit group to said second processing unit group using said main transport path, n holder are supplied from said second loop transport path to said first loop transport path.

8. A sample inspection automation system according to claim 7,
wherein the control section designates a specific unit group from among said plurality of unit groups, and
wherein the processing unit included in said unit group designated by the designation means and the loop transport path supplying holders to the designated unit group is detached.

9. A sample inspection automation system according to claim 5, further comprising a control section which sets an optimal holder count range of the holders to be stopped by said stopper for each of the loop transport paths forming said empty holder transport line.

10. A sample inspection automation system according to claim 9, wherein said control section sets the optimal holder count range based on the type of the processing unit supplied with holders from the loop transport paths and on an operating time zone of said sample inspection automation system.

* * * * *